(12) United States Patent
Göbel

(10) Patent No.: US 7,849,857 B2
(45) Date of Patent: Dec. 14, 2010

(54) TRACHEAL VENTILATION DEVICE

(75) Inventor: Fred Göbel, Wilhelmsfeld (DE)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 767 days.

(21) Appl. No.: 10/556,839

(22) PCT Filed: May 6, 2004

(86) PCT No.: PCT/EP2004/004797

§ 371 (c)(1),
(2), (4) Date: Jan. 12, 2007

(87) PCT Pub. No.: WO2004/101046

PCT Pub. Date: Nov. 25, 2004

(65) Prior Publication Data

US 2007/0095351 A1    May 3, 2007

(30) Foreign Application Priority Data

May 15, 2003   (DE) ................................ 103 21 990

(51) Int. Cl.
*A61M 16/04* (2006.01)

(52) U.S. Cl. ............................ 128/207.14; 128/204.18; 128/207.15; 128/911; 604/103.06; 604/103.07; 604/103.11; 604/104; 606/108

(58) Field of Classification Search ............ 128/207.14, 128/207.15, 207.16, 200.16; 604/103.06, 604/103.07, 103.11, 104; 606/108
See application file for complete search history.

(56) References Cited

U.S. PATENT DOCUMENTS

| 4,502,482 | A  | * | 3/1985  | DeLuccia et al. | 128/207.15 |
| 4,688,568 | A  | * | 8/1987  | Frass et al.    | 128/207.15 |
| 5,188,592 | A  | * | 2/1993  | Hakki           | 604/35     |
| 6,287,290 | B1 | * | 9/2001  | Perkins et al.  | 604/516    |
| 6,526,977 | B1 | * | 3/2003  | Gobel           | 128/207.14 |
| 2003/0000526 | A1 | * | 1/2003  | Gobel        | 128/204.18 |
| 2003/0226566 | A1 | * | 12/2003 | Dhuper et al.| 128/207.15 |

FOREIGN PATENT DOCUMENTS

| DE | 198 45 415 |   | 9/1999 |
| WO | WO 01/34221 | * | 5/2001 |

* cited by examiner

*Primary Examiner*—Justine R Yu
*Assistant Examiner*—Clinton Ostrup
(74) *Attorney, Agent, or Firm*—Dority & Manning, P.A.

(57) ABSTRACT

Tracheal ventilation device, particularly a tracheal tube, which seals the trachea in a substantially air-tight manner. The device includes a cuff that blocks the trachea below the glottis and is traversed by a ventilation cannula. The cuff is larger in its filled, freely displaceable, unrestricted state than in its filled state positioned in the trachea. The cuff is of a flexible soft film material and lies against the trachea by means of its folds. The device is adapted to the morphology of a child's larynx and is available in finely graded sizes.

9 Claims, 8 Drawing Sheets

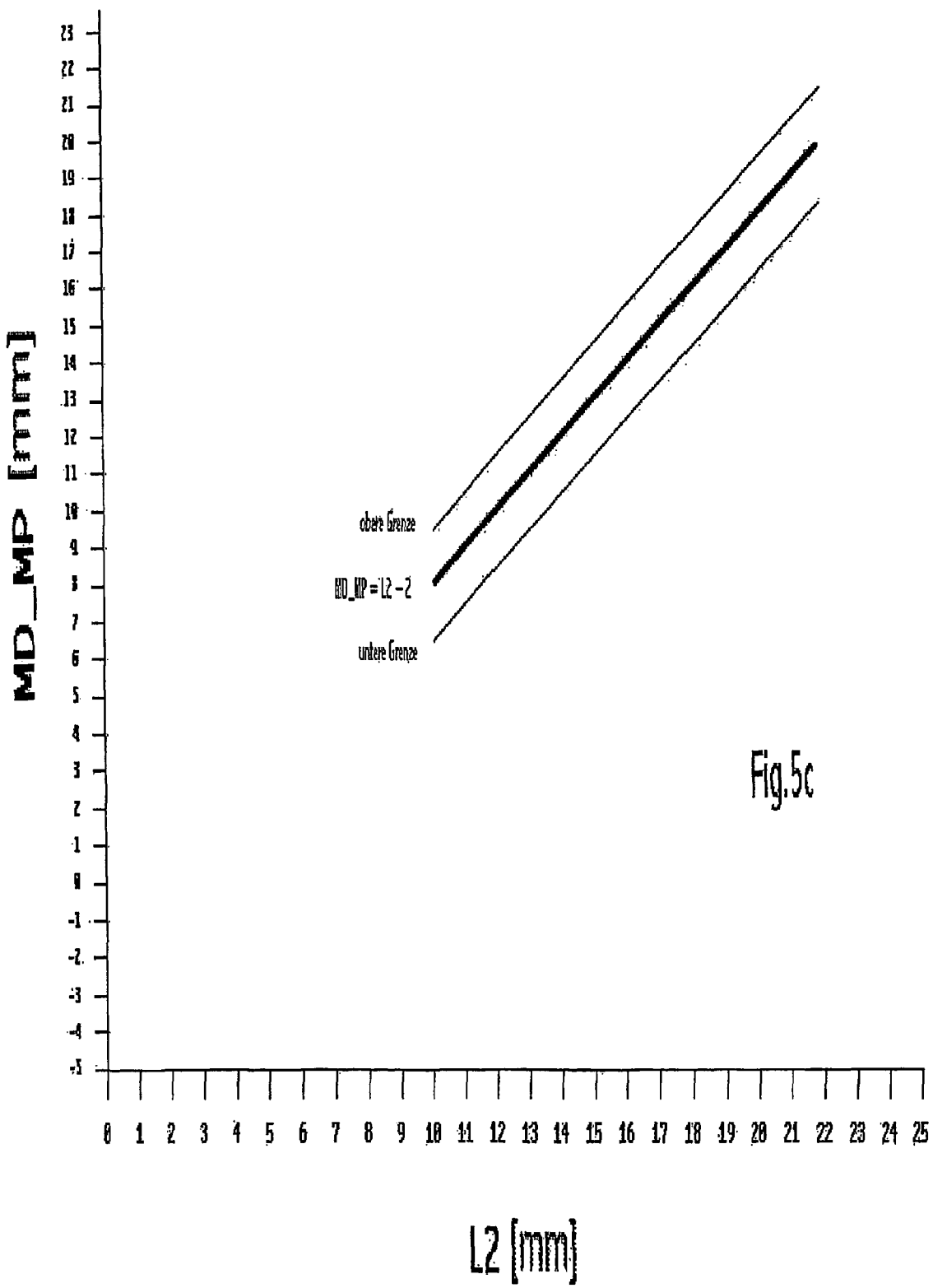

TRACHEAL VENTILATION DEVICE

TECHNICAL FIELD

The invention concerns a tracheal ventilation device, particularly a tracheal tube, which seals the trachea in a manner that is as tissue-compatible as possible during the ventilation of a pediatric patient, comprising a cuff balloon that blocks the trachea below the glottis and is traversed by a ventilation cannula, said cuff balloon being made of a flexible soft film material and being larger in the filled state in which it is freely deployed without restriction than it is in the filled state placed in the trachea, and said cuff balloon lying with its folds against the trachea.

PRIOR ART

DE 198 45 415 A1 describes a tracheal ventilation device in which the cuff balloon (cuff) is made of a flexible soft film material of minimal wall thickness. Such a cuff balloon is well suited for a wide variety of applications in the intubation and mechanical ventilation of patients.

DE 196 38 935 C1 also describes a comparable tracheal ventilation device that can be used in a general manner.

One area in which the use of cuffed ventilation tubes is still problematic is the tracheal intubation of newborns and children. Cuffed pediatric ventilation tubes are considered to be decidedly risky for the patient, since injuries to the trachea and the larynx have been caused time and again by the filling of the cuff balloon. Lesions are usually brought about by the direct effect of the filling pressure of the cuff on the perfusion of the supplying vessels in the tissue adjacent the cuff. The reduced supply, infarction and die-off of the affected tissues and structures can lead to extremely severe, lifelong impairment or to the death of the child.

Ventilation tubes equipped with so-called low-volume/high-pressure cuffs are especially problematic in this connection. In these devices, the diameter of the cuff balloon in the freely deployed, non-intubated state is smaller than the diameter of the trachea to be sealed. To seal the trachea, therefore, the wall of the cuff has to be expanded, usually under high pressure. The expansion pressures that come to be exerted on the adjacent tissue as a result almost always bring about the complete interruption of vascular supply, and, in short order, degeneration of the structures adjacent the cuff.

In the tracheal tubes currently in use, the cuff balloon is preferably fashioned of thin films that are dimensioned to have a residual volume, so-called high-volume/low-pressure cuffs. With these tubes, the diameter of the cuff balloon in the freely deployed, non-intubated state appreciably exceeds the diameter of the trachea to be intubated (with an adequate safety tolerance of usually about 50%). When a high-volume/low-pressure cuff is used to seal the trachea, due to the deployment of the cuff envelope that occurs in the trachea (blocking), there is virtually no expansion of the cuff envelope under the potentially tissue-damaging pressures that are the rule with low-volume/high-pressure cuff balloons. Thus, in tracheal sealing with high-volume low-pressure cuffs, the intentionally produced folding of the balloon envelope permits filling pressures that are compatible with perfusion and provides the user with the certainty that the barometric pressure measured in the cuff balloon largely matches the pressure transmitted transmurally to the tissue. In the intubation of adults, severe tracheal or laryngeal injuries have been successfully reduced to a very low level, even with long-term intubation, through the use of such high-volume cuff balloons with a cuff envelope that is folded in situ.

Problems still remain, however, in attempting to apply the high-volume/low-pressure principle that has proven effective for adults to ventilation tubes for intubating premature infants, newborns, children and toddlers. With the cuff materials currently in wide use, such as PVC, latex and silicone, it is not possible to make residual-volume cuff balloons which in terms of shape and size meet the special requirements of intubating the airways in the child and which can be relied on to behave atraumatically, especially during relatively long-term intubation.

Thus, although it is theoretically feasible from a technical standpoint to give the balloons the type of geometric configuration necessary to ensure low-pressure behavior with the use of conventional materials, because of the specific properties of these materials such cuff balloons are nonetheless unsuitable for pediatric ventilation.

For example, cuff balloons of this kind are, as a rule, manufactured in wall thicknesses of 50 to 100 microns when made of PVC and 100 to 200 microns in the case of silicone and latex. The processing limit of PVC being made into cuff balloons suitable for ventilation (usually by on-line extrusion blow molding) is a critical minimum wall thickness of about 40 to 50 micrometers. If PVC cuffs are made much thinner-walled than this, they carry the risk of focal, nonelastic evagination (herniation) of the cuff wall even under a very slight pressure load (of 20 to 30 mbar, as is usual for tracheal intubation), leading in the worst case to displacement of the distal opening of the ventilation tube by the hernia as it forms and to a much-feared valve effect during ventilation.

Similar considerations apply to the processing of latex into residual-volume balloons with wall thicknesses below 100 micrometers. Since latex-based cuff balloons are produced by dipping, for one thing it is technically difficult to produce thin-walled balloons less than 100 micrometers thick, and for another, in many cases such balloons show inadequate resistance to mechanical stress under ventilation conditions. Moreover, latex-based components are now deemed unsuitable because of their potential allergenicity.

Silicone balloons are also produced by the dipping method, and, for similar reasons, when given a residual-volume type of geometry their usability for pediatric ventilation tubes is limited in a wall thickness range below 100 micrometers.

In configuring a cuff that is dimensioned to have an adequate residual volume, hence a cuff of suitable geometry, the aforesaid minimum wall thicknesses that are necessary with PVC and silicone almost always result in a mechanics or a rigidity for the cuff balloon that largely precludes its atraumatic use with pediatric tracheal tubes. The special design criteria that must be met by a cuff balloon for atraumatic pediatric intubation, such as small radii in the cuff shoulder, a residual diameter, and a cylinder-like conformation of the cuff balloon with a short overall length for the cylinder (cuff), entail a variety of risks for pediatric patients when a cuff is made in this fashion from conventional materials.

Hence, a cuff configured in this way and made of conventional material, dimensioned to render it suitable for a high-volume/low-pressure system and cylindrically shaped, is usually quite prominent as it rests in folds on the tube shaft in the evacuated or unblocked state, and thus becomes a mechanical obstruction during both intubation (insertion of the tube in the trachea) and extubation (removal of the tube). This can lead to reflex-provoking irritations (laryngospasm) of the larynx or vocal folds (glottis) by the bulging cuff envelope resting in folds on the shaft. In many cases, in the evacuated state the envelope of a conventional cuff will also form sharp-edged overlying folds that face the mucosa and can inflict cutting injuries on it, or may even make penetrating cuts into deeper-lying structures, during both intubation and extubation of the cuff.

Moreover, with pediatric cuffs of conventional design, owing to the thickness of the wall material and the resulting rigidity, there is no guarantee in many cases that in the tracheally blocked state pressure will be distributed uniformly from the cuff balloon to the tracheal mucosa. As the folds form in situ, the rigidity of the cuff envelope often causes compression and congestion (bruising) of the mucosa in the area of the gusset-shaped onset—facing the tracheal wall—of the fold in the cuff wall. Moreover, in many cases pressure maxima that are operative transmurally occur in the portions of the balloon that are convex in the direction of the trachea and are located between the invaginated regions of the folds, where, as a focal phenomenon, they can cause critical pressures to be exerted against the adjacent tissue that far exceed the actual filling pressure of the cuff, resulting in proportionate hypoperfusion of the adjacent mucosa (infarction). The filling pressures that such cuffs of conventional design require in order to deploy are already close to the critical perfusion values. The folding pattern assumed in the trachea by a correspondingly shaped cuff balloon made from conventional materials is usually coarse because of the lack of pliability of the cuff envelope, and is not very efficient in sealing against gas emanating from the direction of the lungs (the trachea and the bronchi) and secreta emanating from the direction of the throat. This is problematic especially when the filling pressure of the cuff is exceeded briefly by the ventilatory pressure exerted on the cuff from the direction of the trachea and the bronchi. To create a given seal, the residual-volume cuff of conventional design usually has to be filled at marginally critical pressures from the very beginning and will therefore appreciably exceed those pressures.

Thus, pediatric ventilation tubes with cuff balloons can currently be made from conventional materials only in a functionally inadequate and potentially traumatizing manner. Due to the difficulty or impossibility of reconciling conventional cuff materials with a low-pressure cuff geometry or conformation, the cuff balloons of many pediatric ventilation tubes are currently being designed with an insufficient or nonexistent residuum (low-volume/high-pressure cuff). In other cases, to reduce the rigidity-induced bulging of the cuff envelope on the shaft in the evacuated state and the attendant irritating or traumatizing effect, the cuff is made to deviate appreciably in length from the anatomically and physiologically compatible longitudinal extent. To prevent such bulging, which is likely to occur primarily in the shoulder region of the cuff owing to a particular rigidity, the cuff is often given an approximately spindle shape as an alternative. The residual diameter of the central portion will then be adequate under some circumstances, but the portion stretched into the spindle shape proximal and distal to the central portion usually makes for a potentially traumatizing excessive length for the cuff. In many cases, the proximal portion of such a cuff reaches in situ into the particularly pressure-sensitive so-called subglottic larynx located below the vocal folds (glottis). Upon improper intubation (cuff placed too high in the trachea) and the use of improperly designed tracheal tubes (overlong cuff), lesions of utmost severity and an extremely high likelihood of complication occur in this portion of the child's airways. The subglottic larynx must therefore be considered a particular source of risk in the design of cuffed pediatric ventilation tubes.

Even today, the high overall application risk of conventional cuffed pediatric tubes still prompts the overwhelming majority of users to reject the cuff entirely as a sealing element. This being the case, pediatric ventilation tubes that are not provided with a sealing cuff are dimensioned with respect to outer diameter such that the sealing of the airways against the positive ventilatory pressure is brought about substantially by the shaft of the tube itself. The diameter of the tube shaft is chosen to largely match the diameter of the anatomicophysiological bottleneck of the inferior airways in the child, the so-called cricoid cartilage. A small air leak is usually tolerated by the user in these cases, or is aimed for as a safety factor to avoid dangerous pressure peaks in the child's lungs.

Pediatric tracheal tubes without sealing cuff balloons are disadvantageous for ventilation in many cases, however. Surgery is especially problematic, requiring very constant maintenance of anesthesia (stable ventilatory minute volume) and constant blood gas levels, as is potentially the case, for example, with cardiac or neurosurgical intraoperative ventilation. During intensive care ventilation, spontaneous changes in the position of the child can be associated with sharply fluctuating air leaks and render stable ventilation impossible despite close vigilance. A cuffed tube is also sometimes preferred in heavily bleeding interventions in the head region or in intraoperative antiseptic irrigation of the buccal and pharyngeal cavities, due to the inadequate sealing efficiency of a cuffless tube. Blood, flushed-out debris and secretions from the throat will otherwise find their way largely unimpeded into the distal airways and can significantly complicate the ventilatory course and the course during and immediately after extubation.

DESCRIPTION OF THE INVENTION

The object underlying the invention is to provide a tracheal tube comprising a trachea-sealing cuff balloon that is suitable for long-term, airway-compatible use in children and by means of which the known risk of trauma associated with heretofore-conventional cuffed pediatric tracheal tubes is avoided or decisively reduced.

In a tracheal ventilation device of the kind recited at the beginning hereof, the tracheal tube as fashioned according to the invention is provided and produced, according to a particular age or growth class of the respiratory physiology of the child, with a cuff that is characterized by a specific combination of cuff material and cuff wall thickness and by its dimensioning and positioning on the tube shaft.

The inventive tracheal tube provides an application-safe, atraumatic alternative to the heretofore-preferred principle in pediatric intubation of sealing the airways at the level of the physiological bottleneck in the respiratory passages (the cricoid) with a tube shaft of adapted diameter. Instead thereof, the seal against respiratory gases or against secretions collecting above the cricoid is created by a tracheally placed cuff balloon. With the inventive tracheal tube, the cuff balloon ideally comes to lie in the region of the transition from the distal to the medial third of the trachea, where, by virtue of its particular material properties and dimensioning characteristics, it creates a seal for the trachea at cuff filling pressures (5 to 15 mbar) that are well below the pressure levels of tissue perfusion (30 to 35 mbar). The inventive tube therefore avoids with high probability any cuff-pressure-induced lesions of the adjacent mucosa (compressions, infarctions) of the kind known to occur with conventional cuffed pediatric ventilation tubes, not only in the region of the trachea but also in the region of the subglottic and glottic larynx, which is known to be especially problematic with respect to late sequelae.

Owing to the microthin-walled implementation of the cuff balloon, the inventive tube enables the cuff to be evacuated with almost no bulging, and thereby largely prevents irritation or cutting injuries during intubation and extubation.

The inventive tube is further designed to be able to seal adequately against secretions and reliably against gases when used to effect blocking in the proposed low pressure range (5 to 15 mbar). It is intended, inter alia, to ensure a reliable air seal (self-sealing) at tracheobronchially effective ventilatory pressures (peak and plateau pressures) in excess of the set cuff filling pressure.

The inventive tube is so designed with respect to choice of material and specific dimensioning that in the selection of tube size, which with ventilation tubes generally hinges on the diameter of the shaft, proceeding on the basis of sizes calculated according to the usual mathematical formulas, the user can optionally choose the next-smaller shaft diameter, i.e., one that is 0.5 mm narrower. Even with the optional smaller shaft size, the above non-perfusion-impairing cuff filling pressures are sufficient for creating the tracheal seal under standard ventilation conditions (ventilatory pressure<cuff filling pressure) and for self-sealing the cuff against ventilatory pressures that exceed the cuff filling pressure. The optional choice of a smaller shaft diameter can reduce the potentially traumatizing effect of a tube shaft that is selected to be too large (tissue-damaging relative movements between the cricoid and the shaft, with dangerous swelling of the irritated tissue as a consequence), thus offering additional application safety to the user.

The preferred film material of the cuff balloon is a polyurethane or a polyurethane compound. Alternative candidates are materials that, on the one hand, can be processed in the inventive range of wall thicknesses, and on the other hand demonstrate pressure/volume expansion mechanics similar to that of polyurethane in the desired filling pressure range.

The wall thickness of the film used is 0.015 to 0.005 mm. The preferred wall thickness is less than or equal to 0.010 mm and greater than or equal to 0.005 mm. A wall thickness of about 0.007 mm has been found to be ideal for the inventive atraumatic seal. In this case, the wall thicknesses within the balloon film are preferably so configured that the film is thicker in the shoulder region adjacent the tube shaft than it is in the cylindrical portion immediately adjacent the tracheal mucosa.

The technical implementation of the inventive cuff is explained below on the basis of characteristic relationships between certain parameters that respectively describe the cuff and its placement. The following terms are used in this description: diameter of the cuff when freely deployed and not placed in the trachea (D_CUFF), lower radius (R1) and upper radius (R2) in the shoulder portion of the freely deployed cuff not mounted on the tube shaft, distance between the two transition points from R1 to R2 (L2), spacing of the mounting points of the cuff on the tube shaft (MD_MP), distance from the tip of the tube to the proximal mounting point of the cuff on the shaft (SP_MP), distance from the tip of the tube to the distal mounting point of the cuff on the shaft (SP_MD), inner diameter of the tube shaft (ID), distance from the tip of the tube to the glottic depth marking (SP_GM).

The described size relationships apply to pediatric tracheal tubes with shaft inner diameters of 3.0, 3.5, 4.0, 4.5, 5.0, 5.5, 6.0, 6.5 and 7.0 mm. This size distribution covers the age and developmental classes from newborns to young adults about 15 years of age.

The diameters of the cuff balloon are graduated such that the diameter of the cuff (D_CUFF) ranges from 8 to 22 mm.

In addition to the suitable choice of material and the implementation of the material in a suitable wall thickness, the combination of the following two ratios is substantially decisive in guaranteeing tracheal sealing of the trachea under standard ventilation conditions in a manner that will not impair perfusion and can be tolerated over the long term:

a) The ratio of cuff diameter (D_CUFF) to the spacing of the mounting points of the cuff on the tube shaft (MD_MP), whose hyperbolic curve can be described approximately, across all sizes, by the straight-line function D_CUFF (mm)= $0.75 \times MD\_MP + 4.00$.

b) The ratio of the tip of the tube to the distal mounting point (SP_DM) to the inner diameter of the tube shaft (ID), which is also hyperbolic in shape and can be characterized across all sizes by the straight-line function SP_DM (mm)=$2.36 \times ID - 0.86$.

In dimensioning the inventive tracheal tube, particular attention is given to the fact that the axial longitudinal extent of the cuff mounted on the shaft must be selected to be, on the one hand, as small as possible, in order to maximize the distance between the proximal end of the cuff and the glottis or the glottic placement mark (to reduce the risk of traumatizing the pressure-sensitive subglottic larynx with a cuff transiently dislocated to the glottis); and, on the other hand, as large as is judged to be barely necessary in order to create the inventive trachea-compatible seal of the airways in the described combination of material, wall thickness and further dimensioning of the cuff.

The material being implemented and the cuff being dimensioned and placed on the shaft as taught by the invention, the pressure in the cuff balloon is adjusted so that within a filling range of 5 to 20 mbar, and preferably 10 to 15 mbar, a reliable air seal compatible with the mucosa is created which remains effective even when the pressure built up in the distal airways (the trachea and the bronchi) below the cuff briefly exceeds the filling pressure of the cuff, for example during the plateau phase or the peak pressure phase of a ventilation cycle. This behavior, known as "self-sealing," is made possible by a specific configuration of the cuff. The diameter of the cuff is residually dimensioned (i.e., it exceeds the diameter of the trachea to be sealed) in order to allow the filled cuff to assume a proximally and distally extending, torus-like shape in situ (between the tube shaft and the tracheal wall) (see FIG. 4a). If the ventilatory pressure exceeds the filling pressure of the cuff, the distally convexly oriented bulge of the cuff changes to proximally concave (see FIG. 4b). Due to the low volume expansion behavior of the cuff envelope at the respiratory pressures that can be expected (usually <30 mbar), in this situation, where the ventilatory pressure acting on the cuff is transferred to the cuff filling pressure, the proximal bulge of the cuff does not undergo any appreciable deformation. Instead, the forces transiently developed in the cuff are transferred to the lateral walls (the cylindrical portion) of the cuff or to the trachea immediately adjacent the lateral walls. The cylindrical portion of the cuff nestles against the tracheal wall with a force that corresponds to the ventilatory pressure prevailing at that time, an effect which in the case of relatively high ventilatory pressures (20 to 30 mbar) is usually accompanied by a noticeable jump in the caliber of the trachea in the area adjacent the cuff.

To implement the self-sealing behavior in ventilation situations where the ventilatory pressure intermittently exceeds the filling pressure of the cuff, the inventive tracheal tube exhibits a combination of two further characteristic ratios that permit the shaping in situ of its distal and proximal shoulder portions that is crucial for the self-sealing effect of the cuff balloon.

a) The ratio of the distance between the mounting points of the cuff (MD_MP) to the cuff length of the unmounted, free cuff components, which is expressed by the relation MD_MP=L2−2.

b) The ratio of D_CUFF to radius R1 (R1 describes the radius of the lower circular-arc-shaped transition from the tube shaft to the cuff shoulder), approximated by the relation R1 (mm)= 0.19×D_CUFF+0.39.

The microthin implementation of the cuff envelope gives the filled cuff the necessary dynamics and mechanical properties to enable it to promptly cling to the trachea, changing shape and effecting self-sealing, under variable pressure conditions exerted on the cuff, without undergoing so much elastic deformation (e.g. when the ventilatory pressure transiently exceeds the cuff pressure) that ventilatory gases can escape to a greater extent between the tracheal wall and the cuff.

In addition, with an inventively fashioned cuff in the tracheally blocked state, no compressions of the tracheal mucosa occur in the invaginated region of the cuff folds and no infarctions caused by local pressure peaks occur in the region of contact between the cuff and the mucosa. The gusset-shaped onset region of the folds of the residual-volume cuff envelope is implemented with such a small surface area using the microthin balloon films that it is virtually unable to grab tissue or injure it by squeezing it between the folded portions of the film. In addition, no inhomogeneities can be observed in the force distribution acting on the tracheal wall in the portions of the cuff balloon that are between the invaginated regions when the cuff is blocked, so no focal pressure peaks that might trigger infarctions develop.

Cutting injuries to the mucosa during the insertion and extraction of the tube are also nearly eliminated owing to the microthin wall thicknesses of the cuff, the resultant pliability of its envelope and the nearly total clinging of the evacuated cuff.

The inventive design of the cuff is applicable not only to tracheal tubes, but also to pediatric tracheostomy tubes.

BRIEF DESCRIPTION OF THE DRAWINGS

The appended drawings show an exemplary embodiment of a tracheal tube with a cuff balloon arranged thereon.

Therein.

EXECUTION OF THE INVENTION

Figure 1:
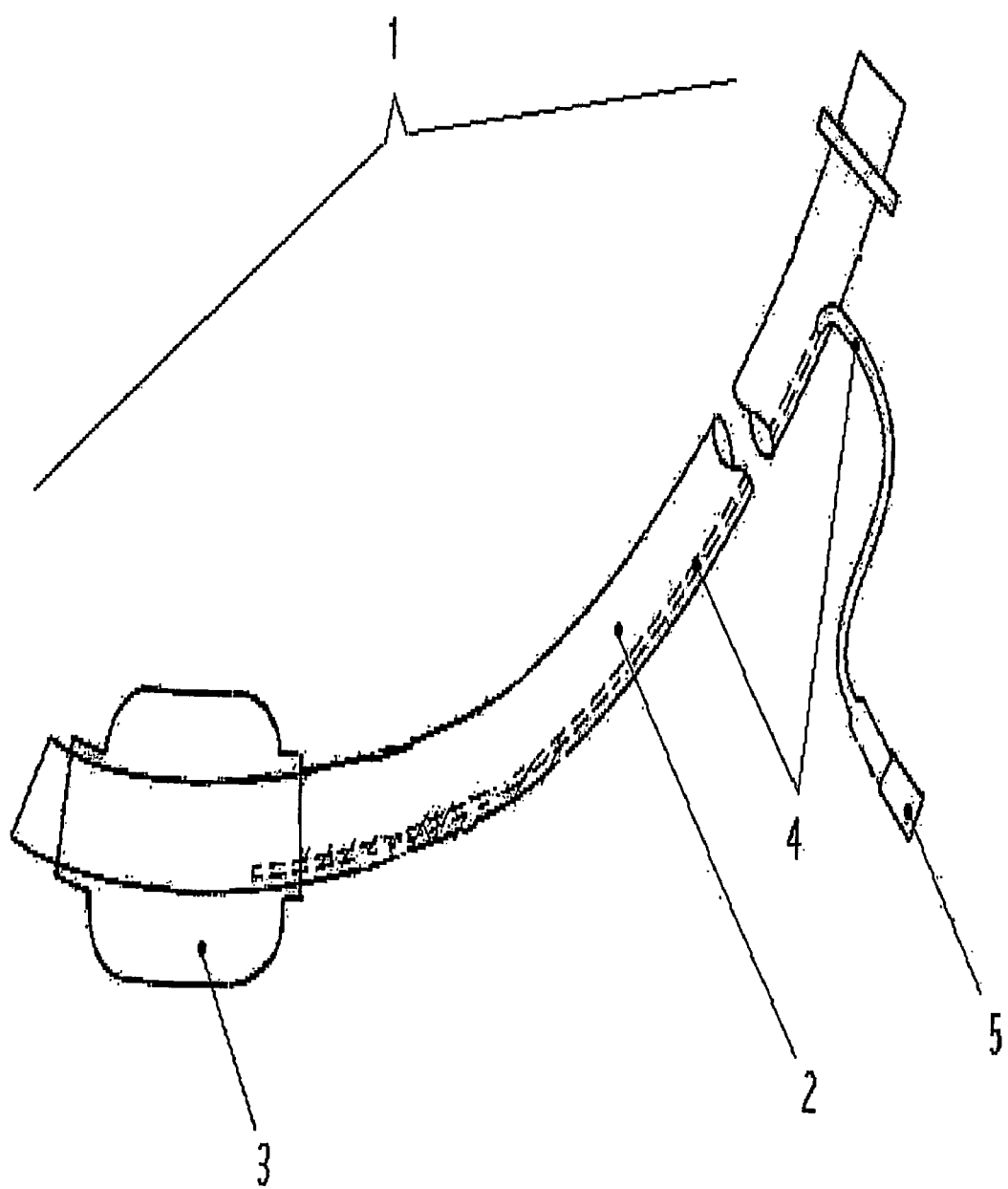
FIG. 1 is a side view of a tracheal tube.

FIG. 1 is a view of a tracheal tube 1. The ventilation cannula 2 is provided with the cuff balloon 3. Via a conduit 4 made in the wall of the cannula 2, the cuff balloon 3 is inflated (blocked) and the introduced air is evacuated (unblocked). For this purpose, conduit 4 carries valve 5 at its end leading out of cannula 2. Tracheal tube 1 is configured with respect to the choice and arrangement of its components in such a way that it guarantees a tissue-compatible tracheal seal in all foreseeable ventilation situations. For optimum performance of this task, tracheal tube 1 is implemented in a plurality of graduated sizes.

Cuff balloon 3 is preferably made of polyurethane, for example of the material Pellethane 2363 supplied by Dow Chemical Inc. This is a high-strength, high-chemical-resistance polyurethane.

The wall thickness of the cuff balloon is 0.015 to 0.005 mm. The wall thickness is preferably implemented as less than or equal to 0.010 mm. The wall thickness of the cuff balloon is ideally about 0.007 mm.

The volume expansion of the envelope of the cuff balloon from the freely deployed, non-intubated, unpressurized state, in which the filling pressure is slightly below atmospheric pressure, to a filling pressure of about 30 mbar is about 5-15%, but preferably no more than 10%.

In terms of its configuration, cuff balloon 3 is individually shaped for the graduated sizes and is fastened to the cannula 2 in an individually typical manner and position. The choice of material and the wall thickness of cuff balloon 3, in combination with the particular geometric conformation of cuff balloon 3, permit the inventive atraumatic sealing of the trachea in which cuff balloon 3 clings to the trachea at an ultra-low filling pressure that does not impair tissue perfusion.

Cannula 2 is fabricated (preferably of PVC) with inner diameters (ID) of 3 to 7 mm (±0.2 mm). The inner diameter is preferably graduated in steps of 0.5 mm in each case. The outer diameters of cannula 2 are adapted to the inner diameters ID and ideally are 4.1 to 9.3 mm (±0.2 mm).

Figure 2:
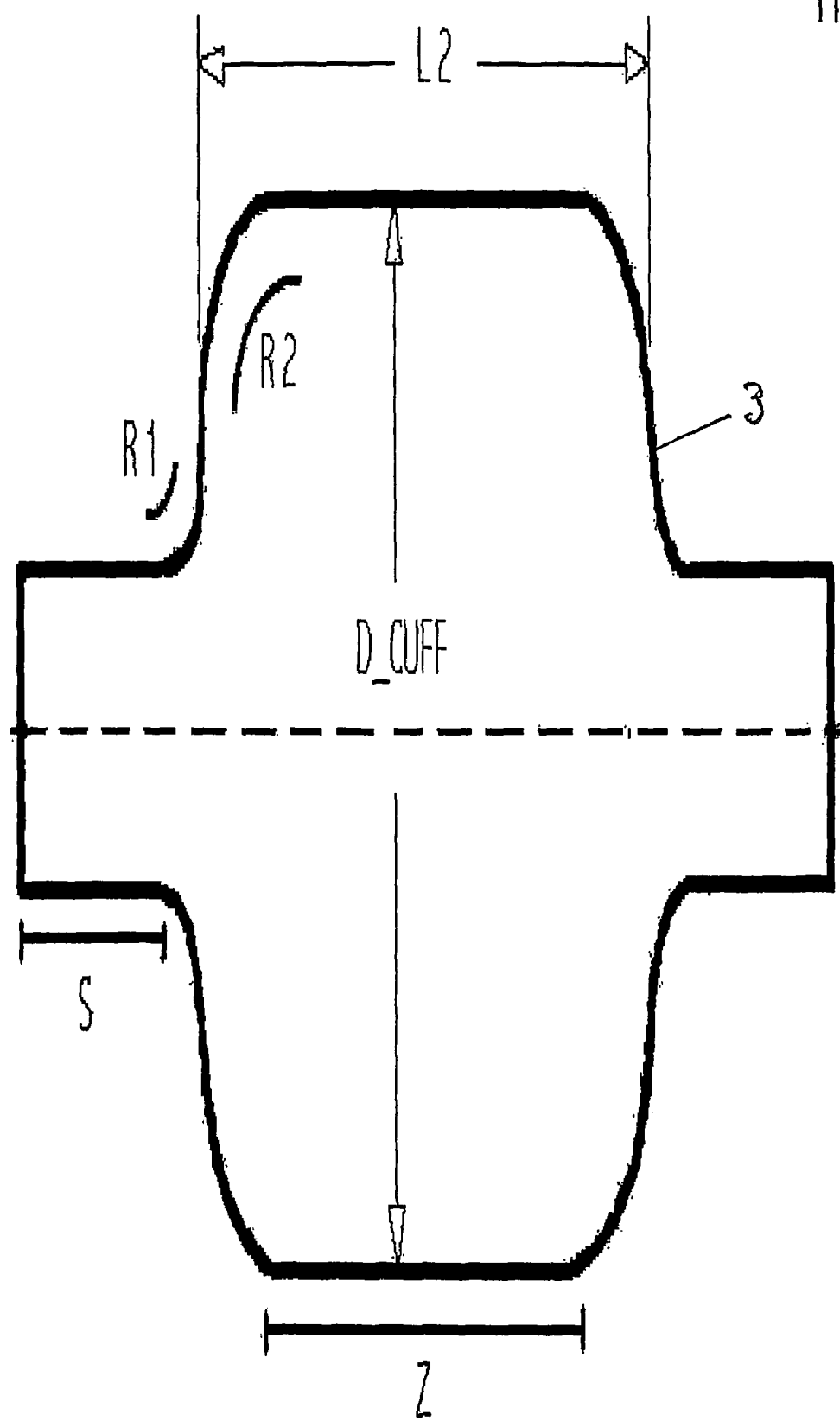
FIG. 2 illustrates the shape of a freely deployed, unmounted cuff balloon in section.

FIG. 2 shows the freely deployed cuff balloon, not yet mounted on the shaft of the tube, as a free-standing component. In the gently inflated state (very slightly above ambient pressure), the following measurements apply across the individual tube sizes. The radial extent of the freely deployed cuff balloon 3 (D_CUFF) is 10 to 20 mm. The axial extent of the cuff balloon is determined by the distance (L2) between the transition points of R1 and R2 in the distal and proximal cuff shoulders. L2 is 10 to 22 mm. R1 expresses the radius of the circular-arc-shaped transition from the shaft portion (S) of the cuff balloon into the cuff shoulder and equals 2.55 to 3.45 mm. R2 denotes the circular-arc-shaped transition from the cuff shoulder (S) into the cylindrical portion (Z) adjacent the tracheal wall. The deviations of the measurements in each case are due primarily to production-related variations in the processing of the polymer or elastomer.

Figure 3:
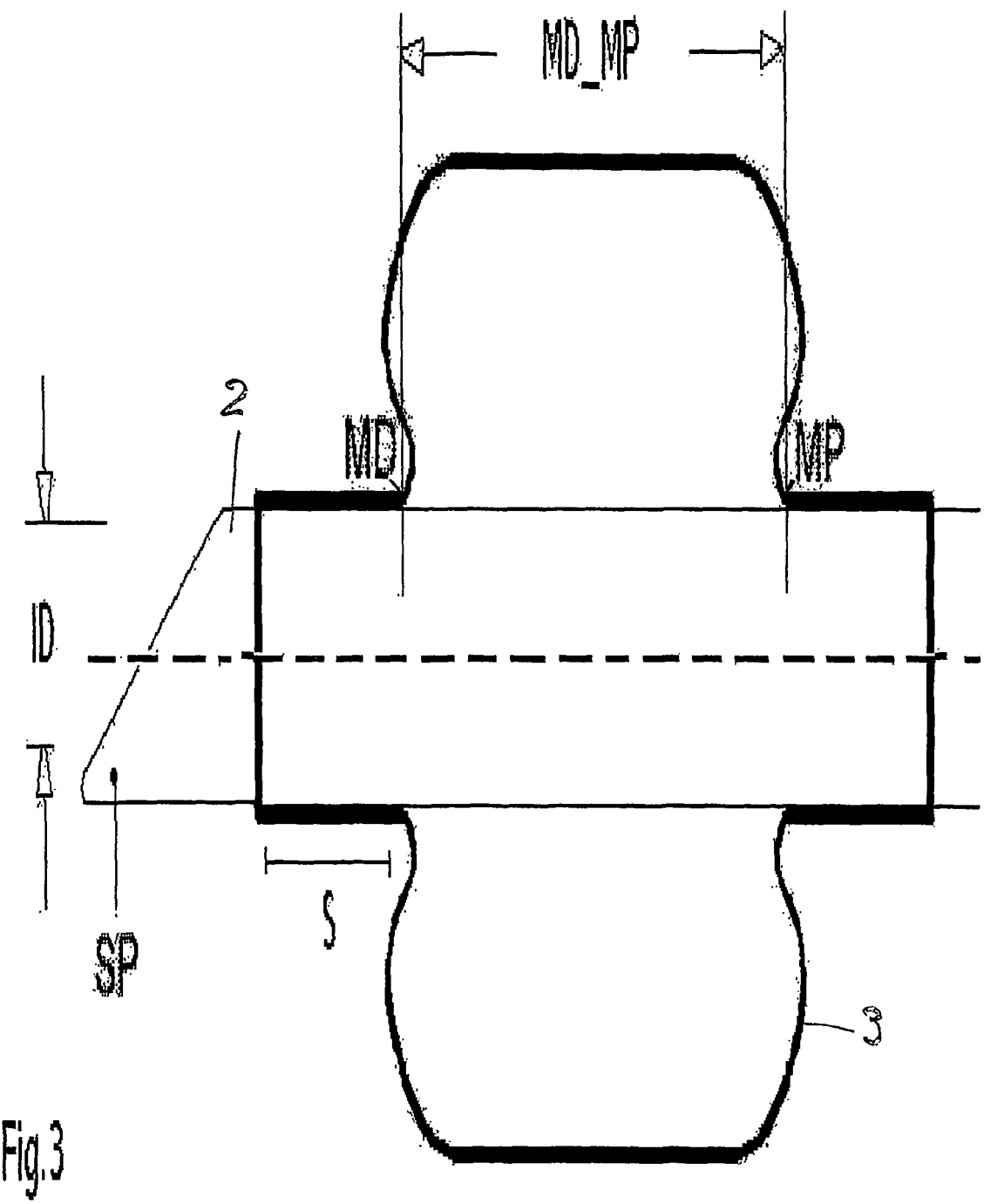
FIG. 3 shows the cuff balloon mounted on the shaft in section.

FIG. 3 depicts the cuff mounted on the tube shaft in a schematic longitudinal section. The cuff balloon 3 is firmly mounted, preferably by adhesive bonding or welding, on the cannula 2 in the region of the shaft portions (S) of the cuff balloon. MD describes the distal mounting point of the cuff balloon on the cannula. The mounting point is defined by the point of the transition from the shaft portion (S) into radius R1 or the positioning of this point on tube cannula 2. MP correspondingly describes the proximal mounting point of the cuff balloon. MD_MP denotes the distance between the two mounting points on cannula 2. MD_MP is equal to 8 to 20 mm (±1.5 mm). The breadth of variation of the mounting dimensions is due primarily to deviations in the mounting of cuff balloon 3 on cannula 2. The end SP of the ventilation cannula (2) that projects beyond the cuff balloon (3) measures 4 to 11 mm.

Figures 4A, 4B:
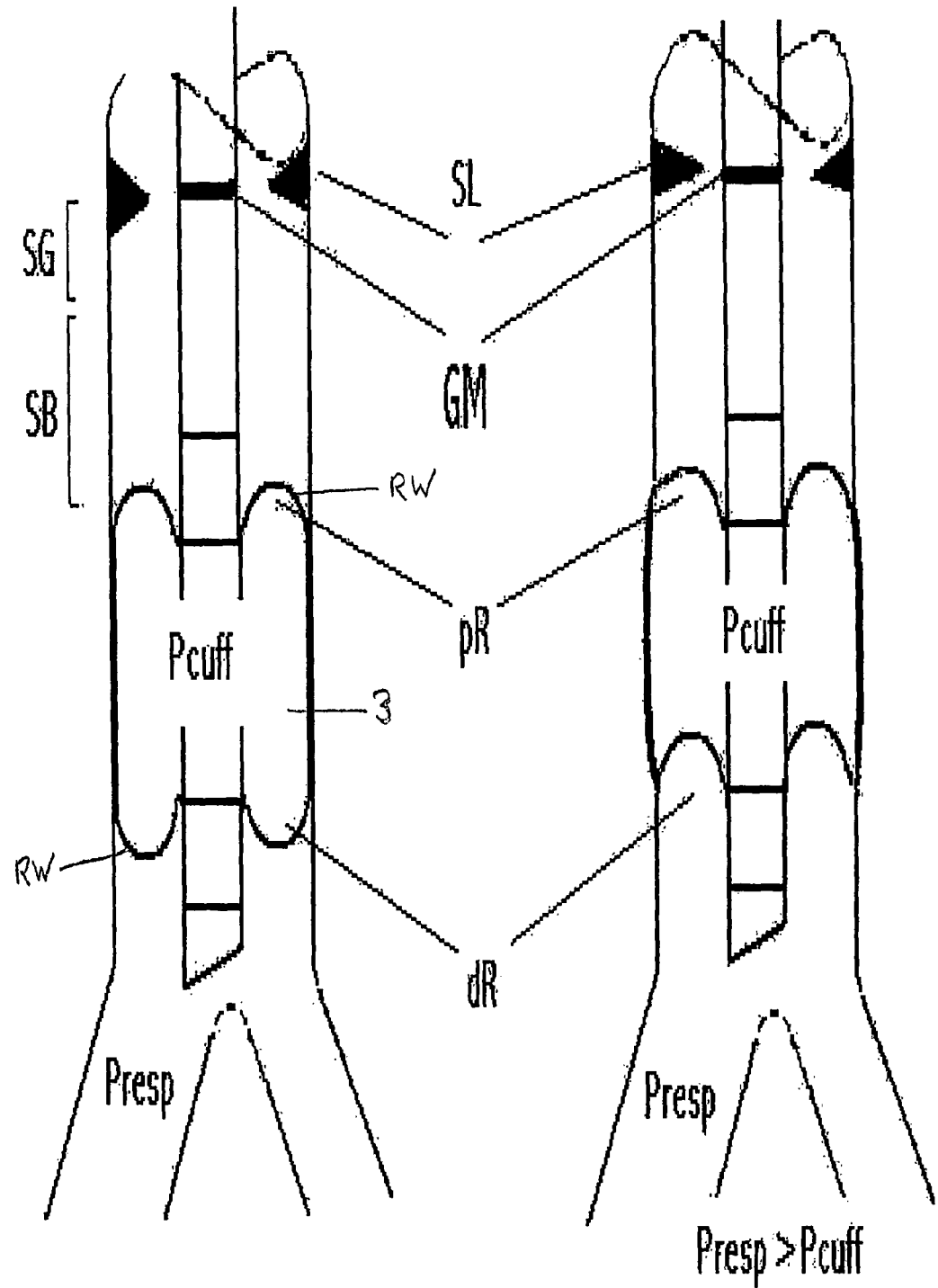
FIG. 4a shows the placement of the tracheal tube in the trachea in section.
FIG. 4b is a schematic representation of the self-sealing function.

FIG. 4a depicts the tracheal tube placed in the trachea. Cuff balloon 3 is placed in the region of transition from the distal to the medial third of the trachea. The glottic marking (GM) on the tube shaft (2) describes the correct placement of the tube in relation to the orientation point normally used for intubation, the vocal folds (SL). SG denotes the so-called subglottic larynx (the subglottis), which is known to be especially vulnerable to pressure. Mechanical irritation of the tissue should therefore be reduced as much as possible in the region of the subglottic larynx. Since changes in position or spontaneous movements of the child can to some extent result in dislocations of the tube or the cuff balloon in the proximal direction, the inventive tracheal tube incorporates a safety region (SB) and places the cuff as far as possible from the subglottic larynx. Despite the minimized longitudinal extent of the cuff balloon, its special shape and material composition guarantee the inventive sealing properties of the tube.

In tracheal blocking of the residual-volume cuff, the residually dimensioned envelope of the cuff balloon assumes longitudinally extending folds. The cuff also forms proximally and distally extending annular bulges (RW) in its shoulder region.

FIG. 4b describes the self-sealing mechanism of an inventive cuff balloon placed in the trachea in ventilation situations where the ventilatory pressure briefly exceeds the filling pressure of the cuff. Whereas the distal annular bulge (dR) goes from convex (FIG. 4a) to concave (FIG. 4b), the proximal bulge (pR) remains unchanged in orientation (convex) and shape (caused by the low volume expansion of the cuff envelope). The pressure variations within the cuff, which synchronously follow the ventilatory pressure, instead lead to a moderate bulging of the cylindrical portion of the cuff envelope onto the tracheal wall and thereby ensure that the seal is largely maintained even in peak pressure situations.

Figure 5A:
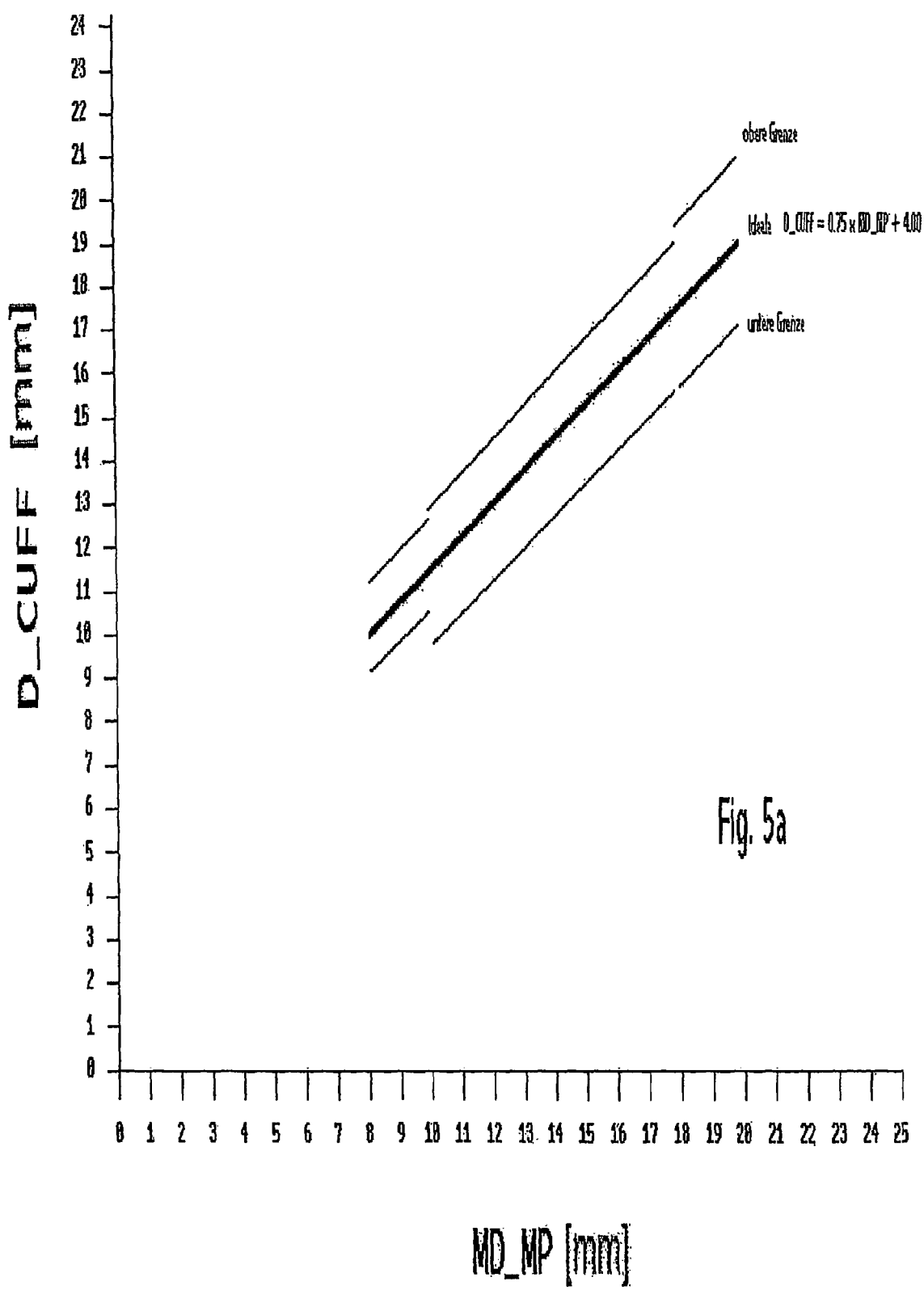
FIGS. 5a-d are graphically descriptive representations of the inventive parameter ratios.

FIG. 5a describes the ratio of D_CUFF to the distance between the mounting points MD_MP of the cuff on the tube shaft. The central straight line (ideal) reflects the approximate relation D_CUFF=0.75×MD_MP+4.00, which applies across all of the tube size ranges (inner diameters of 3.0 to 7.0 mm).

For tubes sized with an inner diameter of 3.0 to 3.5, D_CUFF is defined by a range of values whose upper limit is described by the straight line defined by D_CUFF=0.75×MD_MP+5.00, and the lower limit is defined by the straight line D_CUFF=0.75×MD_MP+3.25.

For tubes of sizes 4.0 to 5.5, a corresponding range of values for D_CUFF obtains, the upper limit being D_CUFF=0.75×MD_MP+5.20 and the lower limit D_CUFF=0.75×MD_MP+2.50.

In the case of tubes of sizes 6.0 to 7.0, C_CUFF obtains as a range of values between the upper limit D_CUFF=0.75×MD_MP+5.50 and the lower limit D_CUFF=0.75×MD_MP+2.50.

MD_MP is assigned a tolerance for mounting variations of about ±1.5 mm across all the tube sizes.

Figure 5B:
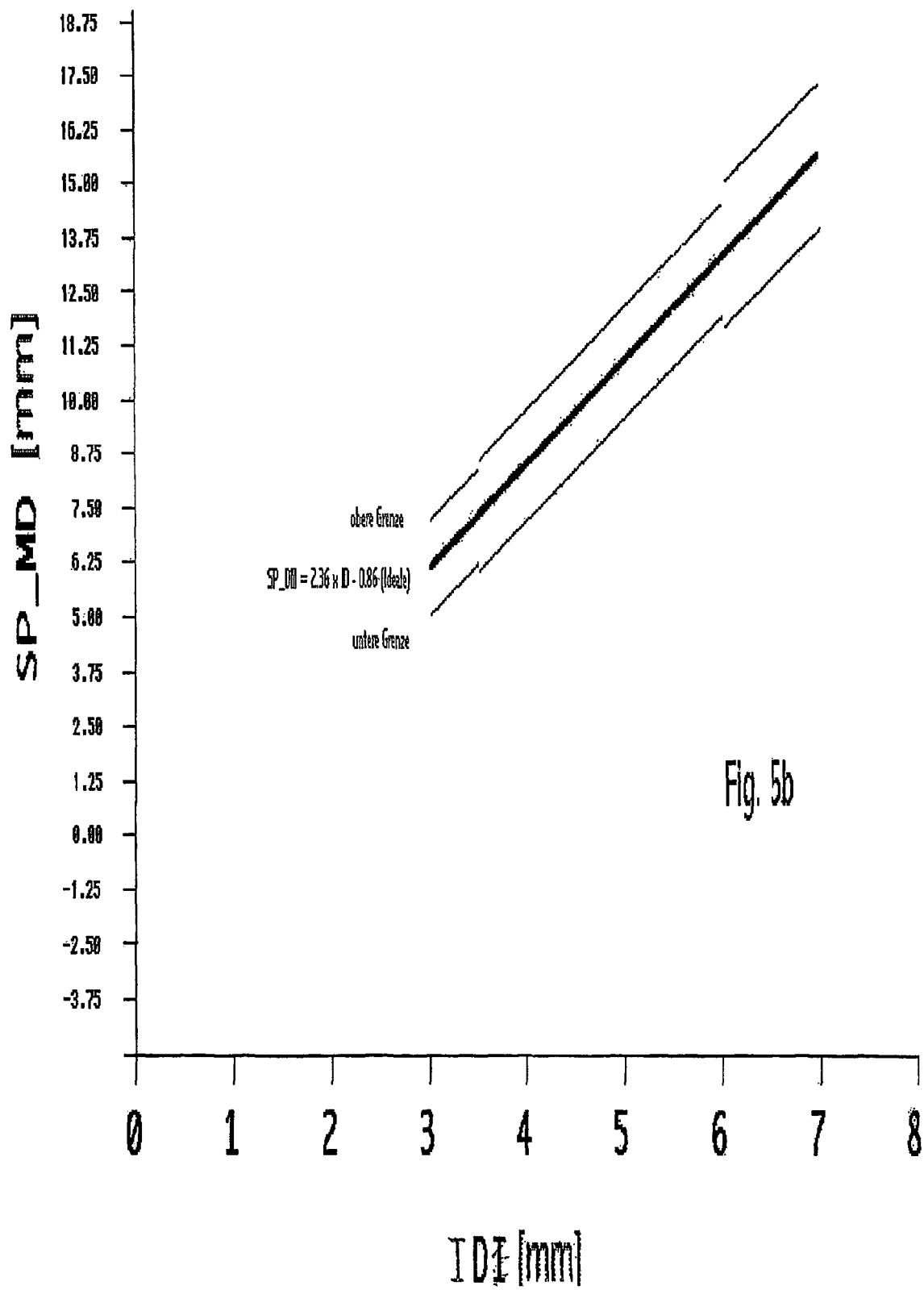

FIG. 5b states the relationship between the shaft inner diameter ID and the distal mounting point SP_MD, which can be approximated across all tube sizes by the straight line (ideal) SP_MD=2.36.times.ID−0.86 mm.

For tubes sized with an ID of 3.0 to 3.5, SP_MD is defined in its upper limit by the straight line resulting from SP_MD=2.36.times.ID−0.11, and in its lower limit by the straight line SP_MD=2.36.times.ID−0.11. For tubes of sizes 4.0 to 5.5, the upper limit for SP_MD obtains from SP_MD=2.36.times.ID+0.34 and the lower limit from SP_MD=2.36.times.ID−2.16. For tubes of sizes 6.0 to 7.0, the upper limit is defined by SP_MD=2.35.times.ID+0.64 and the lower limit by SP_MD=2.35.times.ID−2.46.

Figure 5D:
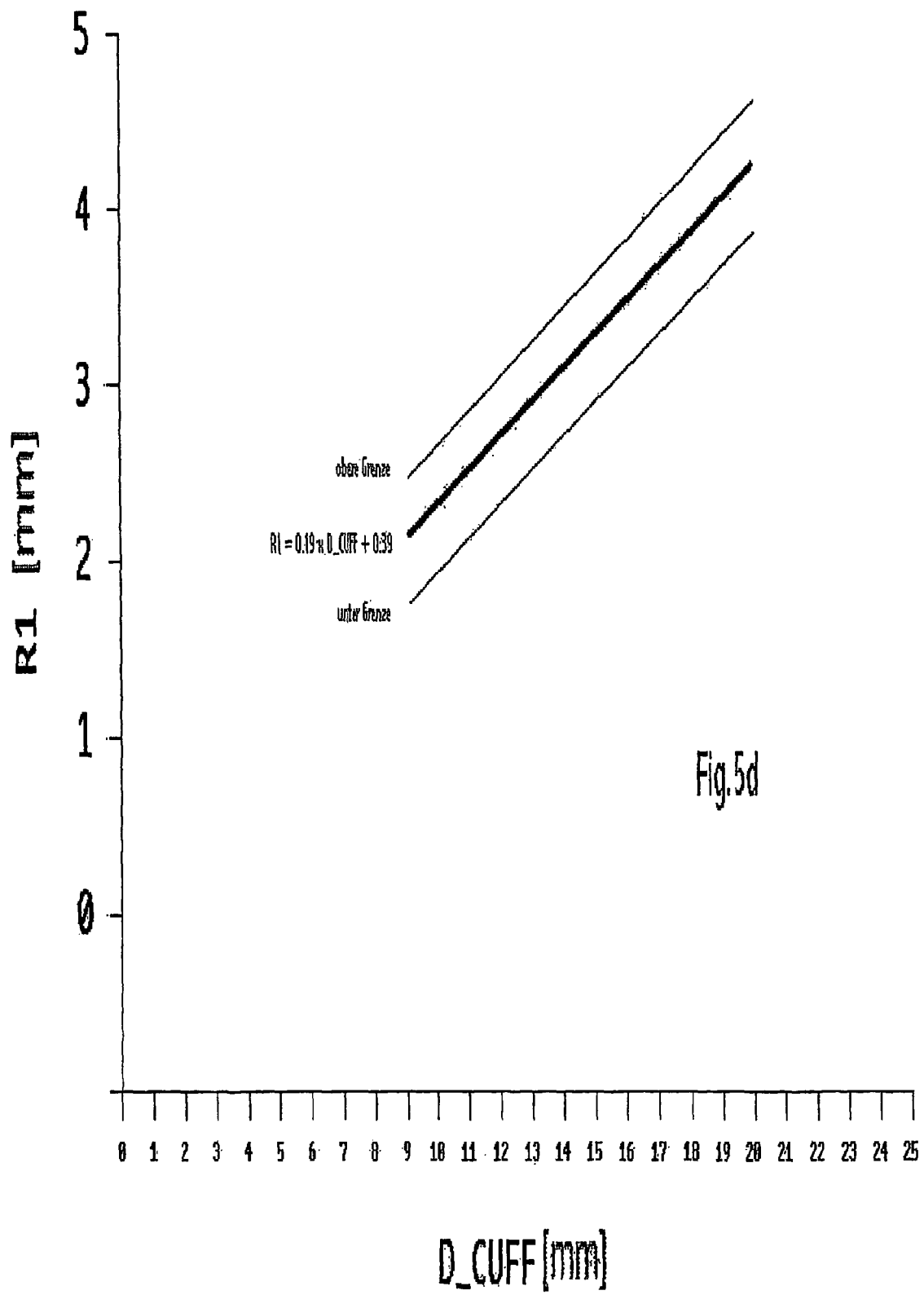
Figure 5A:
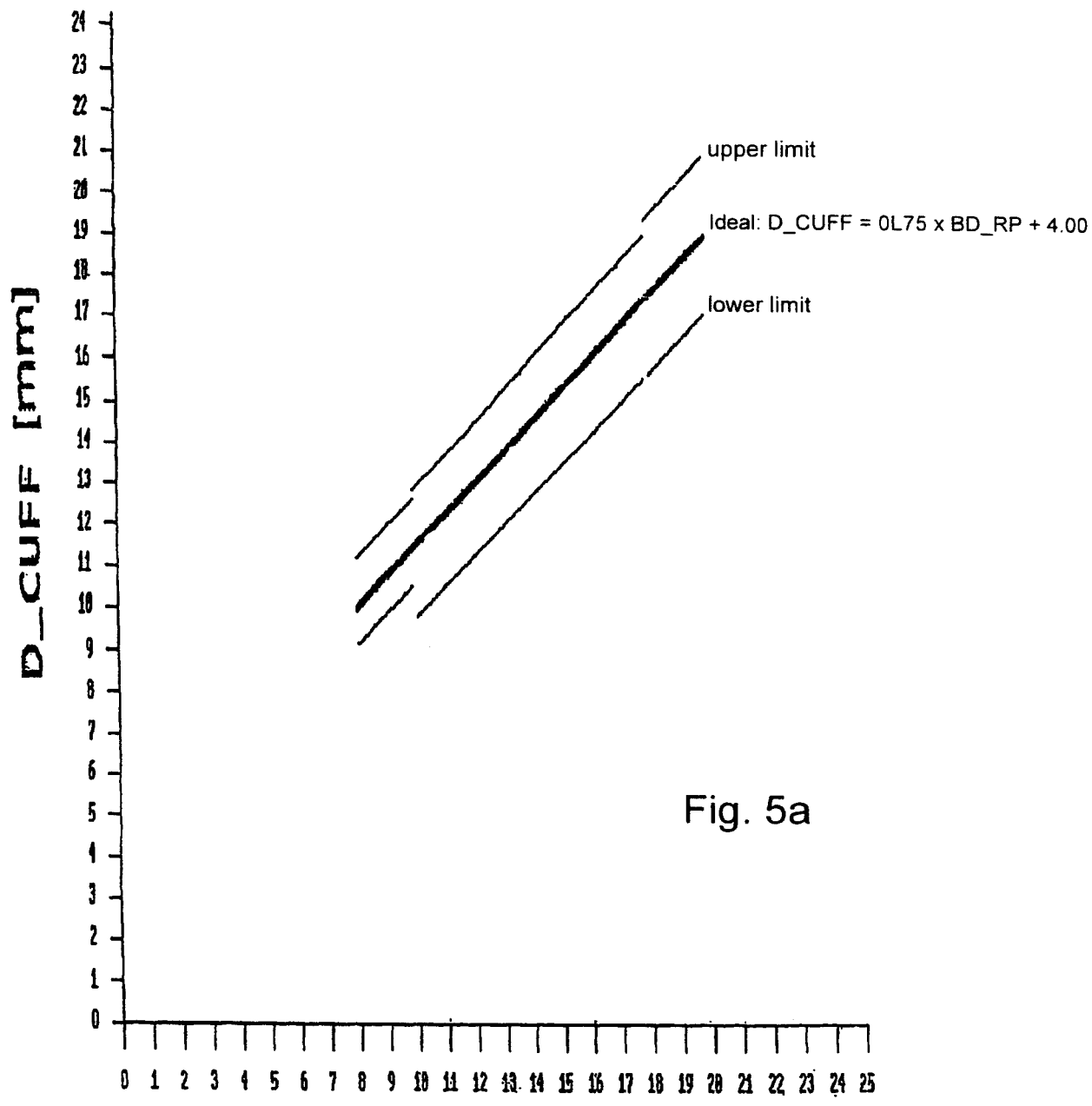
Figure 5B:
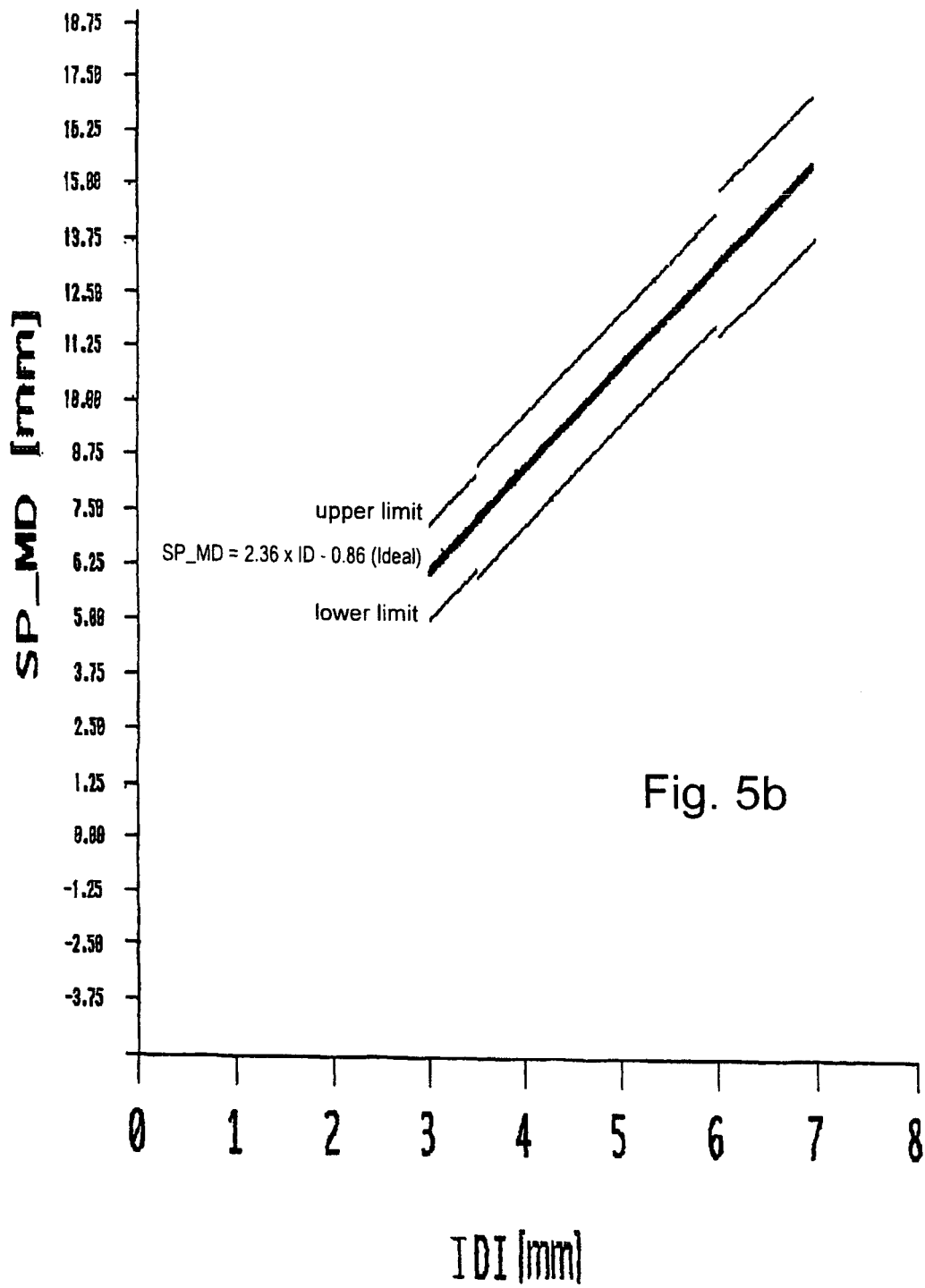
Figure 5C:
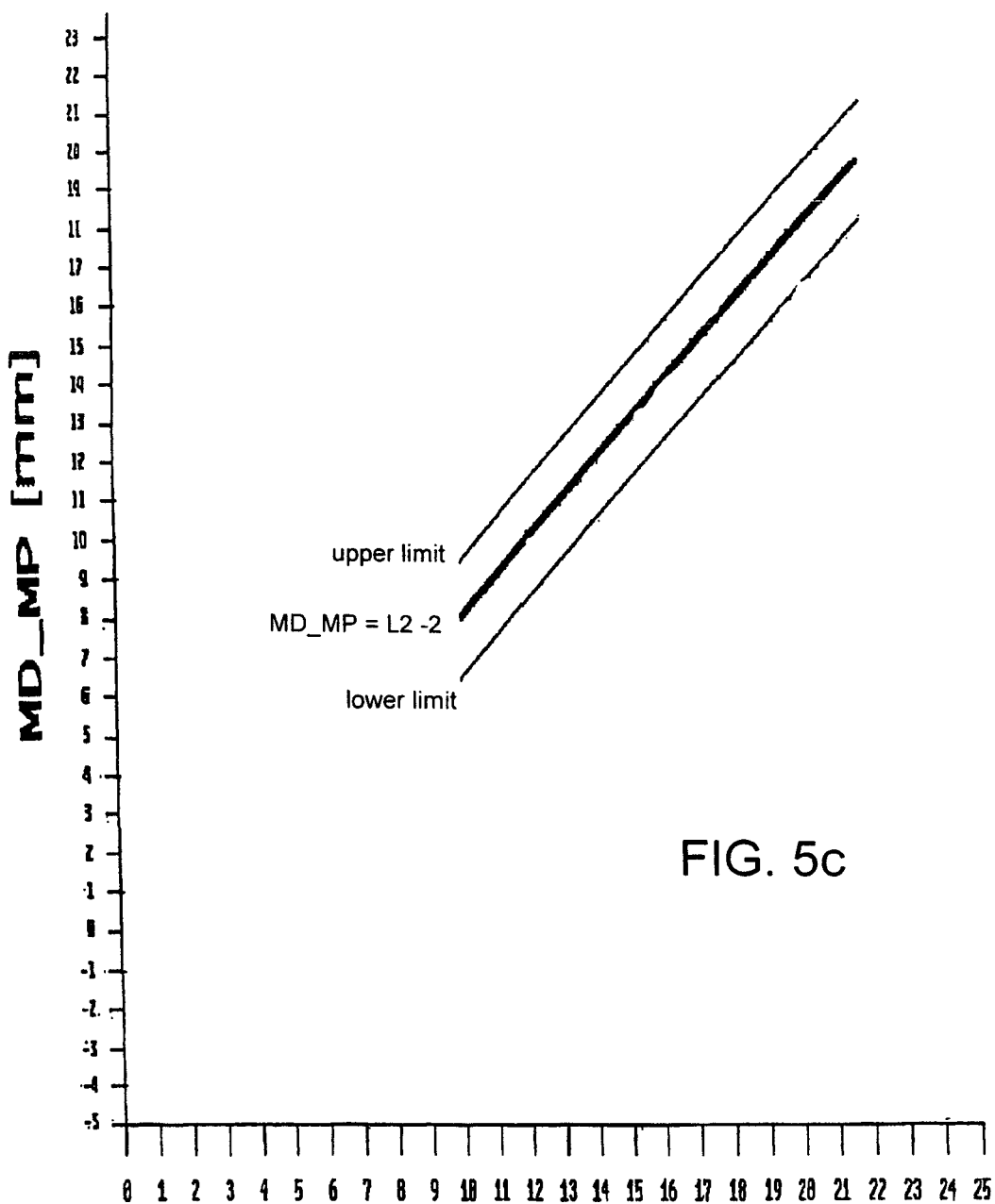
Figure 5D:
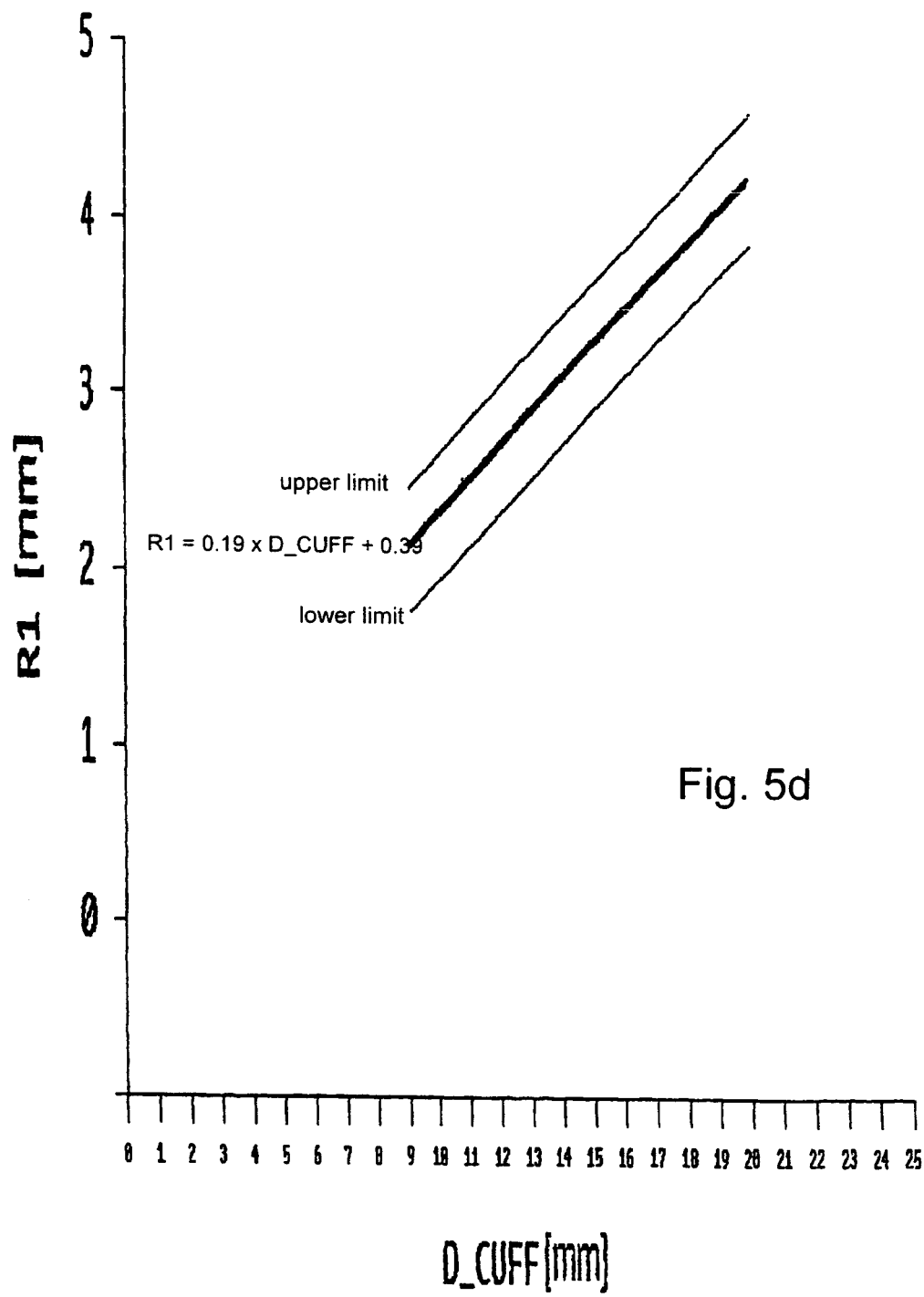

FIG. 5c describes the ratio of the distance between the mounting points of the cuff (MD_MP) to the cuff length of the unmounted, freely deployed cuff component (L2). This ratio can be approximated for all tube sizes by MD_MP=L2−2. The upper deviation limit corresponds, across all sizes, to a straight line defined by MD_MP=L2−0.5, and the lower to a straight line defined by MD_MP=L2−3.5.

FIG. 5d reflects the ratio of radius R1 to the diameter D_CUFF for all tube sizes as the approximation R1=0.19×D_CUFF+0.39. The upper deviation limit corresponds across all sizes to a straight line defined by R1=0.19×D_CUFF+0.69, and the lower to a straight line defined by R1=0.19×D_CUFF+0.09.

What is claimed is:

1. A tracheal ventilation device for sealing a trachea in order to ventilate a pediatric patient, the device comprising:
    a ventilation cannula defining a hollow tube shaft defining a tip at one free end thereof; and
    a cuff balloon that blocks the trachea below the glottis and is traversed by the ventilation cannula, said cuff balloon being made of a flexible soft film material, said cuff balloon in a fully inflated state in which said cuff balloon is freely deployed without restriction having a fully inflated diameter (D_CUFF) being larger than when said cuff balloon is in a filled state placed in the trachea, and said cuff balloon lying with folds against the trachea, MD_MP being the spacing of mounting points of said cuff balloon on the tube shaft;
    wherein for tracheal tubes with shaft inner diameters (ID) between 3.0 mm and 3.5 mm the fully inflated diameter D_CUFF of said cuff balloon has a range of values that lies between straight lines D_CUFF=0.75×MD_MP+5.00 mm and D_CUFF=0.75×MD_MP+3.25 mm and the distance between the tip of the tube and a distal mounting point of the cuff balloon on the tube shaft (SP_MD) has a range of values that lies between straight lines SP_MD=2.36×ID−0.11 mm and SP_MD=2.36×ID−1.86 mm;
    wherein for tracheal tubes with shaft inner diameters (ID) between 4.0 mm to 5.5 mm the fully inflated diameter D_CUFF of said cuff balloon is within a range of values between the straight lines D_CUFF=0.75×MD_MP+5.20 mm and D_CUFF=0.75×MD_MP+2.50 mm and SP_MD lies within a range of values between the straight lines SP_MD=2.36×ID+0.34 mm and SP_MD=2.36×ID−2.16 mm; and
    wherein for tracheal tubes with an inner diameter (ID) of 6.0 mm to 7.0 mm D_CUFF has a range of values that lies between the straight lines D_CUFF=0.75×MD_MP+5.50 mm and D_CUFF=0.75×MD_MP+2.50 mm and SP_MD has a range of values between the straight lines SP_MD+2.35×ID+0.64 mm and SP_MD=2.35×ID−2.46 mm.

2. The tracheal ventilation device in accordance with claim 1 where a wall thickness (D) of the film is 0.015 to 0.005 mm.

3. The tracheal ventilation device in accordance with claim 1, wherein a wall thickness (D) of the film is no more than 0.01 mm.

4. The tracheal ventilation device in accordance with claim 1, wherein the wall thickness (d) of the film in a region of the folds is thinner than in a fold-free region facing a cannula (2).

5. The tracheal ventilation device in accordance with claim 4, wherein said cannula (2) is present with graduated inner diameters (ID) of 3 to 7 mm.

6. The tracheal ventilation device as specified in claim 5, characterized in that the graduation of the inner diameter (ID) is 0.5 mm.

7. The tracheal ventilation device in accordance with claim 6, wherein outer diameters (OD) of said cannula (2), adapted to the inner diameters (ID) thereof, are from 4.1 to 9.3 mm.

8. The tracheal ventilation device in accordance with claim 1, wherein the film of said cuff balloon is made of polyurethane.

9. The tracheal ventilation device in accordance with claim 1, wherein applied to said cannula is a marking (GM) indicating distance from an upper edge of said cuff balloon (3) to a vocal fold.

* * * * *

UNITED STATES PATENT AND TRADEMARK OFFICE
CERTIFICATE OF CORRECTION

| | | |
|---|---|---|
| PATENT NO. | : 7,849,857 B2 | |
| APPLICATION NO. | : 10/556839 | |
| DATED | : December 14, 2010 | |
| INVENTOR(S) | : Gobel | |

It is certified that error appears in the above-identified patent and that said Letters Patent is hereby corrected as shown below:

Delete figs. 5a–5d and substitute therefor the drawing sheets, consisting of figs. 5a–5d as shown on the attached page.

Signed and Sealed this
Sixteenth Day of August, 2011

David J. Kappos
*Director of the United States Patent and Trademark Office*